(12) United States Patent
Lane

(10) Patent No.: US 8,905,229 B1
(45) Date of Patent: Dec. 9, 2014

(54) AIRWAY PRESSURE DEVICE STORAGE SYSTEM

(76) Inventor: Tracy Lane, Warwick, RI (US)

(*) Notice: Subject to any disclaimer, the term of this patent is extended or adjusted under 35 U.S.C. 154(b) by 831 days.

(21) Appl. No.: 13/115,840

(22) Filed: May 25, 2011

(51) Int. Cl.
*B65D 81/24* (2006.01)

(52) U.S. Cl.
USPC ........... 206/210; 206/363; 206/349; 206/207; 220/676; 220/526; 220/524; 220/523; 220/500; 312/213; 312/210; 312/209

(58) Field of Classification Search
CPC .................................................. A61B 19/0248
USPC .......... 206/207, 210, 349, 363, 815; 220/200, 220/500, 505, 523–526, 558, 676; 312/209–210, 213, 223.6
IPC . A47B 81/00, 88/04; A61B 19/02; B65D 81/24
See application file for complete search history.

(56) References Cited

U.S. PATENT DOCUMENTS

| | | | | |
|---|---|---|---|---|
| 3,811,250 A | * | 5/1974 | Fowler, Jr. ...................... 96/422 |
| 3,969,006 A | * | 7/1976 | Brown ....................... 312/234.1 |
| 4,964,523 A | * | 10/1990 | Bieltvedt et al. .............. 220/553 |
| 5,192,121 A | * | 3/1993 | Stutler .......................... 312/212 |
| 5,242,220 A | * | 9/1993 | Sandreth ....................... 312/311 |
| 5,388,570 A | * | 2/1995 | Wassil ..................... 128/200.24 |
| 5,399,007 A | * | 3/1995 | Marconet ...................... 312/209 |
| 5,450,874 A | * | 9/1995 | Hamula ........................ 312/209 |
| 5,975,660 A | * | 11/1999 | Tisbo et al. ................... 312/263 |
| 6,309,239 B1 | * | 10/2001 | Johnston ....................... 439/373 |
| 6,359,217 B1 | * | 3/2002 | Thompson et al. ........ 312/223.6 |
| 2003/0227236 A1 | * | 12/2003 | Brooks ......................... 312/100 |
| 2008/0278041 A1 | * | 11/2008 | Lloyd et al. ................... 312/209 |
| 2009/0179533 A1 | * | 7/2009 | Bochner et al. ............... 312/209 |
| 2010/0218764 A1 | * | 9/2010 | Kwok et al. ............. 128/204.18 |

* cited by examiner

*Primary Examiner* — Mickey Yu
*Assistant Examiner* — Brijesh V. Patel
(74) *Attorney, Agent, or Firm* — Gulf Coast Intellectual Property Group

(57) ABSTRACT

A CPAP mask storage apparatus having a first storage compartment that is hermetically sealed so as to substantially isolate the CPAP mask stored therein from airborne particles. The CPAP mask storage device includes a first panel and a second panel operable to provide access to the interior volume of the first compartment. The first panel and the second panel are configured to have adjacent longitudinal edges having semi-annular cutouts forming an aperture to accept an oxygen supply tube therethrough when the first panel and the second panel are in a closed position. The CPAP mask storage apparatus further includes a second container having a disinfecting liquid stored therein operable to disinfect the CPAP mask. A third compartment is contiguously formed with the first compartment and is operable to receive and store CPAP mask accessories.

6 Claims, 1 Drawing Sheet

AIRWAY PRESSURE DEVICE STORAGE SYSTEM

FIELD OF THE INVENTION

The present invention relates to a storage system for medical devices, more specifically but not by way of limitation, a storage system for a continuous positive airway pressure device (CPAP) that functions to provide a substantially contaminant free interior space for storage of a CPAP when not in use.

BACKGROUND

Millions of individuals suffer from medical conditions that include symptoms such as but not limited to breathing problems. Illnesses such as sleep apnea, respiratory distress syndrome and bronchpulmonary dysplasia have varying symptoms from shallow breathing to general obstruction of the air passage. Sleep apnea patients suffer from at least a partial collapse of the air passages, which limits the amount of oxygen to the lungs. The most common treatment for sleep apnea is to utilize a low positive pressure device that pressurizes the air passages so as to substantially prevent the collapsing thereof.

Most patients utilize a CPAP mask during their sleeping hours to treat sleep apnea and other breathing disorders. The CPAP mask is operably secured to the user's mouth and nose and provides a slightly positive pressure to the user's airways during sleep. When not in use the CPAP mask is typically left on a nightstand or stored in some other manner wherein the device is suspended, for example on a bedpost.

One problem with storing the CPAP mask in the open environment is the opportunity for the CPAP mask to be introduced to air contaminants such as dust as well as bacteria. CPAP masks can often become moist during use and when placed on a nightstand will be in a position to become potentially contaminated with dust and other matter. The contamination matter can potentially be introduced into the air passage of the user during a subsequent use thereof. Currently CPAP masks do not include any type of additional storage compartments or disinfecting apparatus so as to execute a proper storage and cleaning method so as to substantially inhibit the contamination of a CPAP mask.

Accordingly, there is a need for a CPAP mask storage device that provides a substantially contaminant free environment to store a CPAP mask when not in use. Furthermore, the storage device for a CPAP mask should further accommodate the CPAP mask while operably coupled to the air tubing and provide a sterilizing compartment.

SUMMARY OF THE INVENTION

It is the object of the present invention to provide a storage apparatus for a CPAP mask, when the CPAP mask is not in use, that functions to provide an environment that substantially reduces the probability of the CPAP mask becoming contaminated with dust and other airborne particles.

Another object of the present invention is to provide a CPAP mask storage apparatus that can accommodate the CPAP mask while still operably coupled to the air tubing that connects the CPAP mask to the air source.

A further object of the present invention is to provide a CPAP storage apparatus that provides a substantially contaminant free interior volume that includes a keeper configured to suspend the mask within the storage apparatus.

Yet another object of the present invention is to provide a CPAP storage apparatus that further includes an additional interior compartment that is configured to retain a sterilizing solution therein.

Still a further object of the present invention is to provide a CPAP storage apparatus that provides a substantially contaminant free interior volume that is generally rectangular in shape and configured to be suspended on a wall adjacent to a bed.

An additional object of the present invention is to provide a CPAP storage apparatus that further includes an additional compartment configured to receive and store items such as but not limited to filters.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
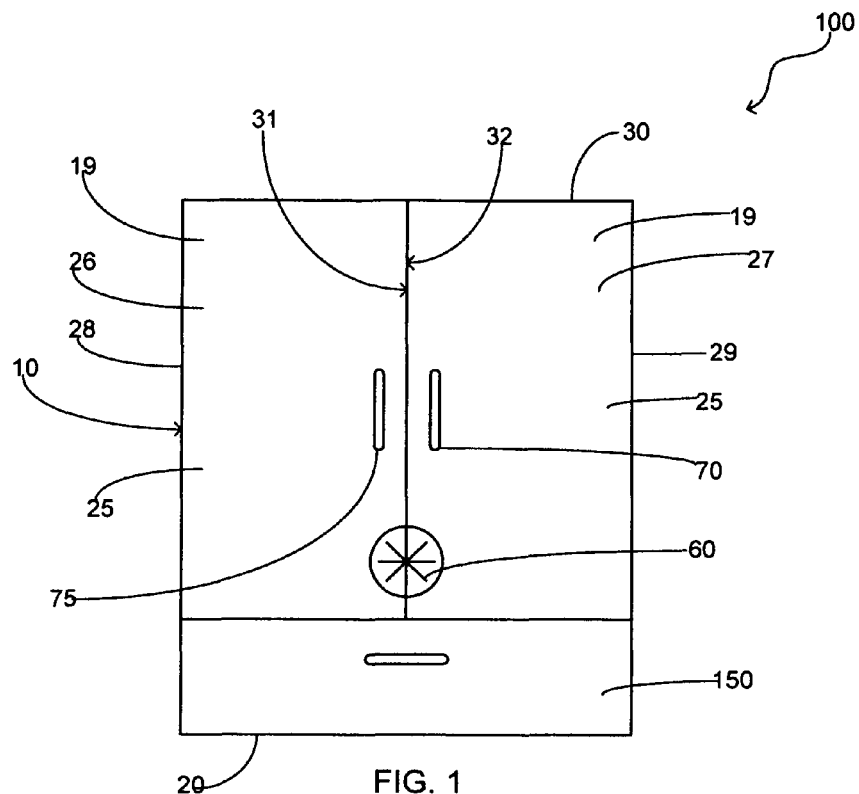
FIG. 1 is front view of an embodiment of the present invention wherein the access panels are in a closed position.

Referring now to the drawings submitted herewith, wherein various elements depicted therein are not necessarily drawn to scale and wherein through the views and figures like elements are referenced with identical reference numerals, there is illustrated a CPAP mask storage apparatus 100 constructed according to the principles of the present invention.

The CPAP mask storage apparatus 100 includes a body 10 having a plurality of walls 15, a bottom 20, front panels 25 and a top 30 defining an interior volume 22 operable to receive and store a CPAP therein. The body 10 is manufactured from a suitable durable material such as but not limited to metal or wood. The body 10 is constructed such that the interior volume 22 is substantially isolated and hermetically sealed from the environment in which the CPAP mask storage apparatus 100 is disposed. The isolated interior volume 22 is important to the CPAP mask storage apparatus 100 in order to prevent accumulation of dust and other airborne particles from propagating into the interior volume 22 while a CPAP mask 99 is disposed therein. While the body 10 is illustrated herein as being generally rectangular, it is contemplated within the scope of the present invention that the body 10 cold be constructed with alternate quantities of walls 15 in order to create body 10 of many different shapes. Additionally, while no particular size of body 10 is required, good resultants have been achieved by utilizing a body 10 that is approximately eight inches in width, ten inches in height and three inches in depth.

The front panels 25 include a first panel 26 and a second panel 27 that are hingedly attached along perimeters 28, 29 respectively. Those skilled in the art will recognize that numerous types of hinges or similar mechanical fasteners could be utilized to hingedly attached the first panel 26 and second panel 27. While not illustrated herein, it is contemplated within the scope of the present invention that the front panels 25 further include a sealing member disposed on the interior surface 24 that facilitates a hermetic seal with the body 10 in order to substantially isolate the interior volume 22. The first panel 26 includes a longitudinal inner edge 31 that is adjacent the longitudinal inner edge 32 of the second panel 27 when the front panels 25 are in the closed position. Integrally formed in the longitudinal inner edge 31 is cutout 40. The cutout 40 is proximate the lower end 37 of the first panel 26. The cutout 40 is semi-annular in shape and further includes a segmented membrane 41 that substantially covers the opening 43.

A second cutout 50 is integrally formed into the longitudinal inner edge 32 of the second panel 27. The second cutout 50 is proximate the lower end 47 of the second panel 27. The second cut-out 50 further includes a segmented membrane 41 that is secured within the second cut-out 50 utilizing suitable durable techniques such as but not limited to chemical adhesion. In the closed position, the front panels 25 are aligned such that the first cutout 40 and the second cutout 50 are substantially aligned and form an annular aperture 60 as shown in particular in FIG. 1. The annular shaped aperture 60 functions to allow an oxygen tube that is operably coupled to the CPAP mask 99 to be journaled therethrough in order to prevent obstructing the front panels 25 from being placed in a closed position wherein the front panels 25 engage the body 10 and create a hermetic seal therewith. Subsequent an oxygen tube being journaled through the annular aperture 60, the segmented membrane 41 biases against the tubing in order to facilitate a substantially sealed connection therewith. The segmented membrane 41 allows the CPAP mask storage apparatus 100 to maintain a substantially hermetic seal even during the event that the user has chosen to leave an oxygen tube engaged with the CPAP mask 99 disposed within the interior volume 22. The segmented structure of the segmented membrane 41 functions to allow the segmented membrane 41 to maintain a biased contact against the exterior surface of different sizes and shapes of oxygen tubes and similar accessories of CPAP masks 99.

While the preferred embodiment illustrated herein utilizes a first cut-out 40 and a second cut-out 50 forming a generally annular aperture 60, it is contemplated within the scope of the present invention that an aperture could be formed in numerous different shapes having a sealing membrane associated therewith in order to accommodate a tube therethrough. It is further conteomaplted within the scope of the present invention that the annular aperture 60 could be formed in numerous different sizes so as to accommodate a variety of diameters of tubing.

Fastened to the exterior surface 19 of the front panels 25 are a first handle 70 and a second handle 75. The first handle 70 and second handle 75 are generally proximate the longitudinal inner edges 31, 32 and provide an interface to transition the front panels 25 between their closed and open positions. Those skilled in the art will recognize that the first handle 70 and second handle 75 could be formed in numerous different shapes and sizes.

Secured to the rear wall 14 within the interior volume 22 is a keeper 80. The keeper 80 is generally arcuate in shape and functions to engage a portion of the strap 98 of the CPAP mask 99. The keeper 80 is manufactured from a suitable durable material such as but not limited to metal. The keeper 80 functions to suspend the CPAP mask 99 adjacent to the rear wall 14. Those skilled in the art will recognize the numerous styles of mechanical fasteners cold be utilized to construct the keeper 80 in order to maintain the CPAP mask 99 in a suspended position adjacent the rear wall 14. While the keeper 80 is illustrated herein as being secured to the rear wall 14, it is further contemplated within the scope of the present invention that the keeper 80 could be secured to the inner surface of the top 30.

Disposed within the interior volume 22 of the body 10 and integrall formed therewith is a container 110. The container 110 is generally square in shape having a plurality of walls 112, bottom 114 and removable top 116 forming an interior volume. The container 110 is configured so as to receive and store therein a liquid such as but not limited to a sanitizing disinfectant liquid. The container 110 has an interior volume of sufficient size to accommodate a CPAP mask 99 therein. The removable top 116 further includes handle 118. The container 110 functions to store a disinfecting liquid facilitating the cleaning of the CPAP mask 99 so as to substantially prevent growth of bacteria thereon. It is contemplated within the scope of the present invention that the container 110 could be formed in numerous different shapes and perform the desired functionality as described herein. Furthermore, it is additionally contemplated within the scope of the present invention that the container 110 could be a flexible liquid proof bag that is suspended on the rear wall 14. The container 110 is provided for either regular or intermittent use by the user in order to substantially disinfect the CPAP mask 99.

A second compartment 150 is included with the CPAP mask storage apparatus. The second compartment 150 includes and interior volume that is sufficient in size to accommodate CPAP mask 99 supplies such as but not limited to air filters and other supplies therein. It is contemplated within the scope of the present invention that the second compartment 150 could be configured in numerous different configurations and accomplish the desired objective described herein. While no particular configuration is required, good results have been achieved by utilizing a second compartment 150 that is configured as a drawer. While the CPAP mask storage apparatus 100 is illustrated herein as having a second compartment 150, it is further contemplated within the scope of the present invention that the CPAP mask storage apparatus 100 could have additional compartments for storage of accessories associated with breathing treatment devices.

Figure 2:
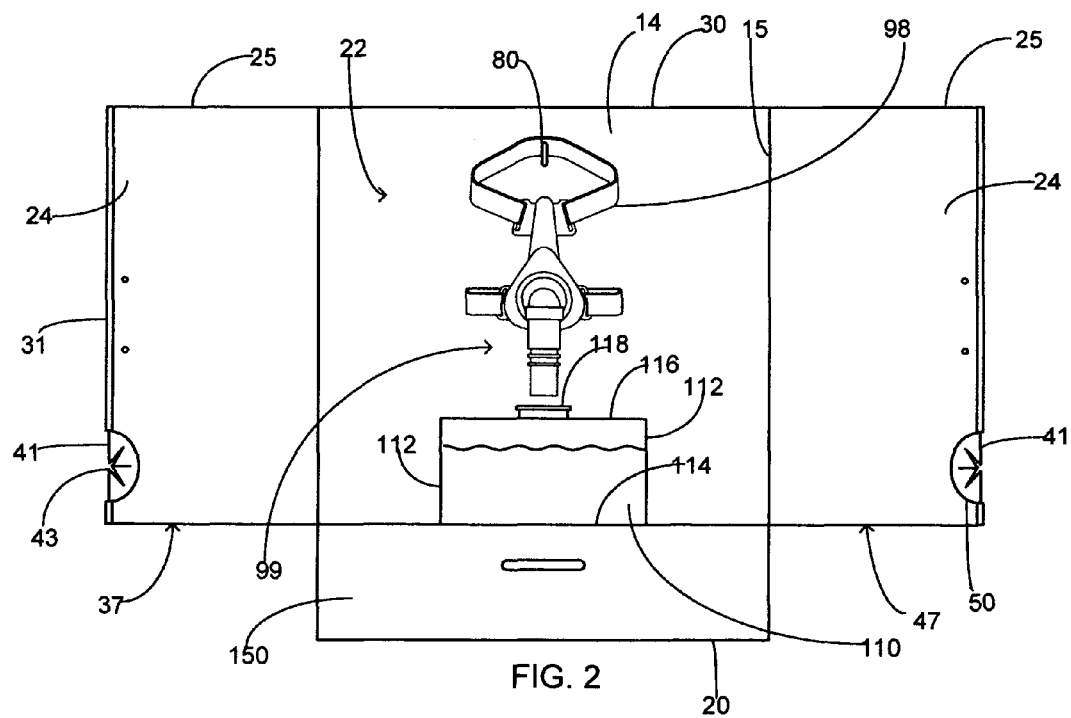
FIG. 2 is a front view of an embodiment of the present wherein the access panels are in an open position.

Referring in particular to FIGS. 1 and 2, a description of the operation is as follows. In use, subsequent a breathing treatment or a use of a CPAP mask 99 the user will grasp the first handle 70 and second handle 75 and transition the front panels 25 to their open position. Ensuing the front panels 25 being transitioned to an open position, the user will place the CPAP mask 99 within the interior volume 22 and engage a portion of the mask strap 98 with the keeper 80 so as to maintain the CPAP mask 99 in a suspended position along the rear wall 14. The user will then return the front panels 25 to a generally closed position wherein the interior volume 22 is hermetically sealed substantially inhibiting any airborne particles from contacting the CPAP mask 99. If the user kept the CPAP mask 99 engaged with an oxygen supply tube, during the placing of the front panels 25 to their closed position the user would position the oxygen supply tube such that it will journal through the annular aperture 60 wherein the segmented membrane 41 engages the outer surface of the oxygen supply tube and remains in a biased position thereagainst so as to inhibit any passage of airborne particles into the interior volume 22. Additionally, the user can utilize the container 110 to disinfect the CPAP mask 99. The user will place the CPAP mask 99 within the interior of the container that has a disinfecting liquid disposed therein so as to provide a cleaning routine prior to suspending the CPAP mask 99 on the keeper 80.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A CPAP mask storage apparatus comprising:
   a first compartment, said first compartment being generally rectangular in shape, said first compartment including a plurality of walls, a bottom and a top defining an opening providing access to an interior volume, said opening being rectangular in shape, said opening having a perimeter edge, said interior volume of said first compartment configured to be substantially atmospherically isolated from the environment of the CPAP mask storage apparatus;
   a first panel, said first panel being operably secured to said first compartment and positioned to cover a first portion of said opening, said first panel being hingedly attached to said first compartment proximate said perimeter edge, said first panel further including an inner longitudinal edge, said inner longitudinal edge further including a first cutout, said first cutout being semi-annular in shape, said first panel having a first position and a second position;
   a second panel, said second panel being operably secured to said first compartment and positioned to cover a second portion of said opening, said second panel being hingedly attached to said first compartment proximate said perimeter edge opposite said first panel, said second panel further including an inner longitudinal edge, said inner longitudinal edge of said second panel having a second cutout, said second cutout being semi-annular in shape, said second panel having a first position and a second position;
   a second compartment, said second compartment disposed within said first compartment, said second compartment having a plurality of walls, a bottom and a top configured to define an interior volume, said top configured to be removable to provide access to said interior volume of said second compartment, said second compartment having a liquid therein; and
   wherein subsequent said first panel being placed in said first position and said second panel being placed in said second position, said interior volume of said first compartment is hermetically sealed so as to substantially inhibit airborne particles from propagating thereinto.

2. The CPAP mask storage apparatus as recited in claim 1, wherein said first cutout and said second cutout are adjacent each other forming an annular aperture subsequent said first panel and said second panel being placed in said first positions.

3. The CPAP mask storage apparatus as recited in claim 2, further including a sealing membrane, said sealing membrane secured to said first cutout and said second cutout, said sealing membrane further including a plurality of portions, said sealing membrane operable to maintain a substantially hermetic seal of said interior volume of said first compartment.

4. The CPAP mask storage apparatus as recited in claim 3, further including a keeper, said keeper being arcuate in shape, said keeper secured within said interior volume of said first compartment, said keeper operable to suspend a CPAP mask within said interior volume of the first compartment.

5. The CPAP mask storage apparatus as recited in claim 1, wherein the liquid disposed within said second compartment is a disinfectant.

6. The CPAP mask storage apparatus as recited in claim 5, further including a third compartment, said third compartment being adjacent and contiguous said first compartment, said third compartment having an interior volume.

* * * * *